United States Patent [19]

Yamamura et al.

[11] 4,287,420

[45] Sep. 1, 1981

[54] STEREOSCOPIC X-RAY DEVICE

[75] Inventors: Toshio Yamamura; Takeshi Muraki, both of Yokohama, Japan

[73] Assignee: Toshiba Corporation, Kawasaki, Japan

[21] Appl. No.: 81,127

[22] Filed: Oct. 2, 1979

[30] Foreign Application Priority Data

Nov. 2, 1978 [JP] Japan .............................. 53-134460

[51] Int. Cl.$^3$ .......................... H05G 1/00; H05G 1/30
[52] U.S. Cl. ..................................... 250/402; 250/404
[58] Field of Search ............... 250/313, 314, 402, 404; 313/57, 60

[56] References Cited

U.S. PATENT DOCUMENTS

| 2,110,604 | 3/1938 | Langhans | 250/402 |
|---|---|---|---|
| 2,942,126 | 6/1960 | Silbermann | 313/60 |
| 3,250,916 | 5/1966 | Rogers | 250/314 |
| 3,452,203 | 6/1969 | Shiga et al. | 250/404 |
| 3,857,039 | 12/1974 | Franke et al. | 250/402 |
| 3,962,583 | 6/1976 | Holland et al. | 250/402 |

OTHER PUBLICATIONS

Dol et al., "Application of Longitudinal Magnification Effect to Magnification Stereoscopic Angiography: A New Method of Cerebral Angiography", Neuroradiology, Aug. 1977, p. 395.

Primary Examiner—Alfred E. Smith
Assistant Examiner—Janice A. Howell
Attorney, Agent, or Firm—Schuyler, Banner, Birch, McKie & Beckett

[57] ABSTRACT

A stereoscopic X-ray device used for stereoscopic radiography generates X-rays from a pair of X-ray focal spots. The X-ray device is provided with an evacuated envelope, an X-ray target within the evacuated envelope, and a cathode structure having at least two pairs of filaments. The first pair of filaments form relatively large size X-ray focal spots on the target. The second pair of the filaments form relatively small size X-ray focal spots on the target and are situated between the first pair of filaments on the cathode structure. As a result of these two pairs of focal spots on the X-ray target, a relatively small X-ray device can be used to provide magnification of stereoscopic images of high stereo quality.

9 Claims, 8 Drawing Figures

STEREOSCOPIC X-RAY DEVICE

BACKGROUND OF THE INVENTION

This invention relates to a stereoscopic X-ray device used for magnification stereoscopic radiography.

A stereoscopic image of an object can be obtained by viewing two radiographs on film, a fluourescent plate or an image intensifier with a stereo viewer. Each of the radiographs contains an exposure corresponding to a focal spot on an X-ray target. The focal spots on the X-ray target are separated by a distance. A stereoscopic image is produced because there is a slight difference in the exposures on the two radiographs.

A stereoscopic X-ray tube is a well known device for generating X-ray radiation from two focal spots as described in U.S. Pat. No. 3,250,916 issued to Rogers on May 10, 1966. This tube comprises an evacuated envelope, a cone-shaped X-ray target and a pair of cathodes facing the target. Two electron beams emitted by the cathodes bombard the surface of the target to form two X-ray generating focal spots. These focal spots are separated by a distance on the surface of the target which is equivalent to the interpupillary distance. Radiographs are produced by exposing film to the X-rays alternately generated by different focal spots. The film is positioned in contact with the back of the object. The technique disclosed in the Rogers patent for producing stereoscopic images is called the contact stereo technique.

In order to enhance the stereo effect, the two focal spots on the surface of the target can be separated by more than the interpupillary distance. In practice, the two focal spots should be separted by a distance greater than one tenth the distance between the focal spot and the film. In other words, the two focal spots must be separated by more than 100 mm if the distance between the focal spot and the film is 1 meter. If a separation of 100 mm is desired, a rotating target diameter greater than 100 mm, for example 150 mm, is required for the stereoscopic X-ray tube because of the inclination of the cone-shaped target surface to the cathode. Consequently, to enhance the stereo effect, a large X-ray tube may be necessary. Of course, a large X-ray tube requires a large sized X-ray shield housing which is difficult to handle for radiography.

The enhanced stereo effect for the contact stereo technique discussed above can be obtained by radiographic magnification stereo techniques using two focal spots separated by a relatively small distance. This magnification stereo technique is described in an article entitled "A New Method of Cerebral Angiography", Neuroradiography Vol. 124, Aug. 1977 (Doi et al). This article describes a system which obtains the same depth perception as the contact stereo technique by using two focal spots which are separated by a relatively small distance. The focal spots are smaller than the focal spots in the contact stereo technique. However, the structure of the stereoscopic X-ray tube is not described in this article.

SUMMARY OF THE INVENTION

The object of this invention is to provide a stereoscopic X-ray tube of relatively small size which obtains a large stereo effect. The other object of this invention is to provide a stereoscopic X-ray tube which obtains improved stereoscopic image quality.

The further object of this invention is to provide a stereoscopic X-ray tube for obtaining fast movable stereo images.

According to one aspect of this invention, a stereoscopic X-ray device is provided comprising an evacuated envelope, an X-ray target within the envelope, and a cathode structure for generating at least two pairs of electron beams directed onto the target. The X-ray focal spots generate X-rays. The cathode structure comprises at least two pairs of filaments emitting the electron beams and a focus electrode focusing the electron beams. The first pair of the filaments emits relatively large current electron beams to form relatively large size X-ray focal spots on the target. The second pair of the filaments emits relatively small current electron beams to form relatively small size X-ray focal spots situated between the first pair of focal spots.

BRIEF DESCRIPTION OF THE INVENTION

DETAILED DESCRIPTION OF THE PREFERRED EMBODIMENT

Figure 1:
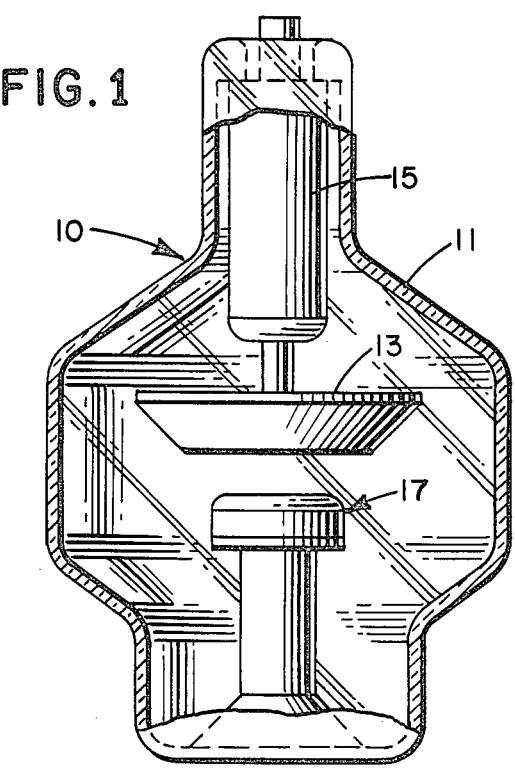
FIG. 1 is an axial sectional view of one embodiment of this invention.
Figure 2:
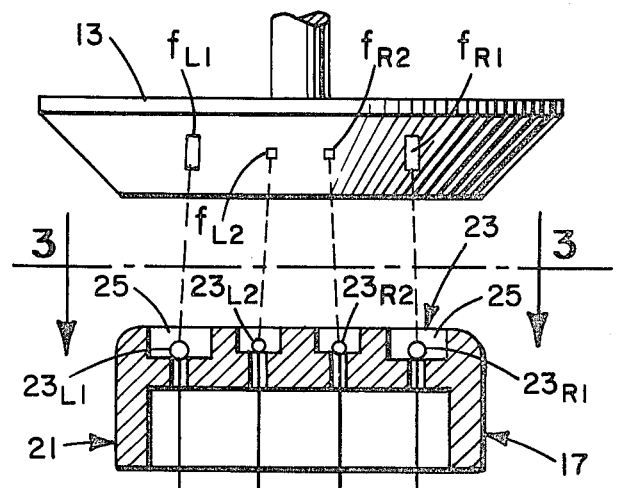
FIG. 2 is a sectional view of the main portion of the stereoscopic X-ray tube shown in FIG. 1.
Figure 3:
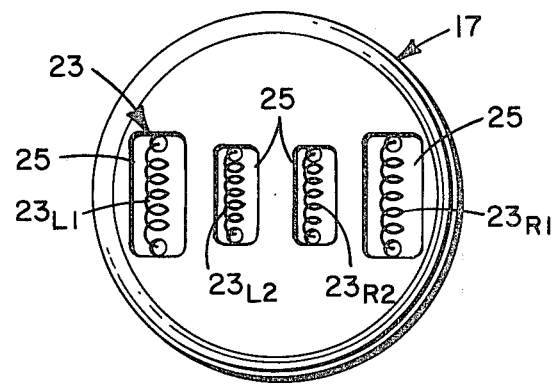
FIG. 3 is a top view taken on line 3—3 of FIG. 2.

Referring now to the drawings, wherein like reference numerals designate identical corresponding parts in each of the embodiments, FIG. 1–FIG. 3 show the stereoscopic X-ray tube 10 of this invention. The tube 10 comprises an evacuated glass envelope 11 which encloses an X-ray target 13 with a rotor 15 in one end thereof and a cathode 17 in the other end. The X-ray target 13 is the anode of the stereoscopic X-ray tube. The rotor 15 is attached to a supporting axis 19 for rotation therewith. On operation, an outside inductive device (not shown) rotates the rotor 15 and the target 13 at high speed about the axis 19. The X-ray target 13 is shaped like a disc plate having a shallow cone shape to cause X-ray radiation to radiate outwardly from the tube envelope.

The cathode structure 17 comprises a cup-shaped focus electrode 21 and two pairs of filaments 23 facing the target 13. On the surface of the focus electrode 21, there are four cavities 25 in which the two pairs of filaments 23 are mounted as shown in FIGS. 2 and 3. The cathode structure 17 generates a plurality of X-ray focal spots ($f_{L1}$–$f_{L2}$ and $f_{R1}$–$f_{R2}$) in a line of X-ray focal spots on the surface of the target 13. Each focal spot corresponds to one of the filaments 23. For example, $f_{L1}$ corresponds to $23_{L1}$, $f_{L2}$ corresponds to $23_{L2}$, $f_{R2}$ corresponds to $23_{R2}$ and $f_{R1}$ corresponds to $23_{R1}$.

The filaments $23_{L1}$ and $23_{R1}$ form a first pair of filaments which generate a pair of focal spots of the same size on the surface of the target 13. On applying a high voltage across the target 13 and the filaments 23, an electron beam is emitted from each of the filaments 23, for example filament $23_{L1}$ of the focus electrode 21, to bombard the surface of the target 13. Consequently, the filament $23_{L1}$ generates the focal spot $f_{L1}$ on the target 13 to radiate X-rays. Similarly, filament $23_{R1}$ generates the focal spot $f_{R1}$ to radiate X-rays.

The other filaments $23_{L2}$ and $23_{R2}$ form another pair of filaments which generate the focal spots $f_{L2}$ and $f_{R2}$ on the surface of the target 13. The focal spots $f_{L2}$ and $f_{R2}$ are smaller in size than the focal spots $f_{L1}$ and $f_{R1}$. The focal spots $f_{L2}$ and $f_{R2}$ also are situated inside the focal spots $f_{L1}$ and $f_{R1}$. The different sizes of focal spots are produced by varying the size of the filaments 23 as illustrated in FIG. 3.

In general radiography, magnification images can be easily obtained by positioning the object relative to the focal spot or keeping the object at a certain distance from the film. The smaller the size of the focal spot used in magnification radiography, the larger the magnification factor (M). In the case of direct radiography on film, the maximum information is obtained by increasing the magnification factor and decreasing the focal spot size. For example, if the magnification factor is 1.5, 2 and 5, the focal spot size is 0.3 mm, 0.1 mm and 0.05 mm, respectively. On the other hand, where the focal spot size is greater than 0.5 mm, to 0.6 mm, the quantity of information is reduced.

Figure 8:
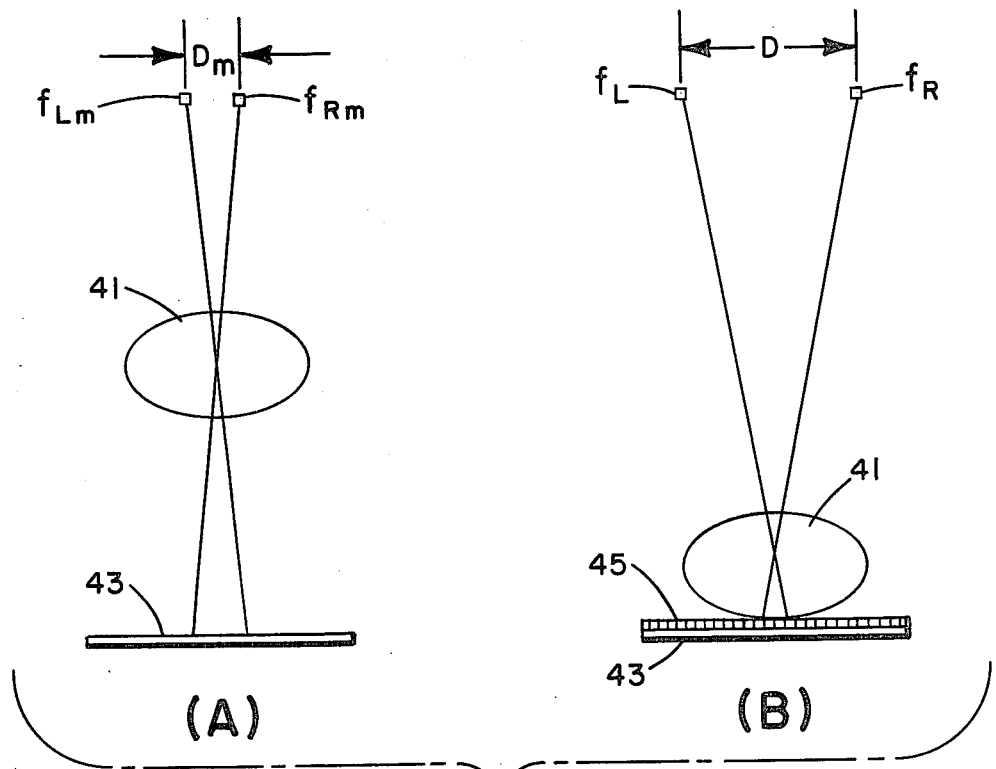
FIG. 8 is a diagram illustrating the operation of this invention where (a) illustrates the contact radiographic technique and (b) illustrates the magnification radiographic technique.

In the magnification radiography system as shown in FIG. 8(a), the relationship of stereo effect or depth perception Z to magnification factor M, the distance $D_m$ between the focal spots ($FL_m$-$R_m$), and constant K is shown by the following equation:

$$Z = KM^2 D_m$$

The equation indicates that the stereo effect Z is proportional to the square of the magnification factor M. If the stereo effect Z is the same in the magnification radiography system and the contact stereo system of FIG. 8(b), and the magnification factor M is doubled, the distance between the focal spots $D_m$ in the magnification radiography system may be about one fourth the distance D between the focal spots $f_L$-$f_R$ in the contact stereo system shown in FIG. 8(b). Furthermore, in the magnification radiography system, the object 41 is situated halfway between the focal spots and the film 43. A grid 45 is used in the contact stereo system to absorb scattered radiation.

Therefore, according to the present invention, large magnification is achieved by a pair of small sized focal spots and a small distance between the pair of focal spots. Upon operation of the X-ray tube shown in FIGS. 1–3, a current first passes through the filament $23_{L1}$ to generate electron beams which bombard the surface of the target 13 to radiate X-rays from the bombarded position, i.e., the focal spot $f_{L1}$. Consequently, the first X-ray image is radiographed. The second X-ray image is continuously radiographed by X-rays from the focal spot $f_{R1}$. The radiographs are observed through a stereo viewer. In the same way, a pair of radiographs are obtained by X-ray exposures from both the focal spots $f_{L2}$ and $f_{R2}$. The radiographs produced by X-rays from large size focal spots $f_{L1}$ and $f_{R1}$ are suitable for thick objects or quickly moving objects and the radiographs produced by X-rays from small size focal spots $f_{L2}$ and $f_{R2}$ are suitable for observing objects in detail.

The plurality of focal spots on the surface of the target 13 are generated by switching the filament current among the filaments 23 of focus electrode 21. The switching time for switching the filament current for each of the filaments is about 0.5 sec. to 1.5 sec. As a result, an object under observation must be essentially stationary for a period of time approximately equivalent to the switching time.

Figure 4:
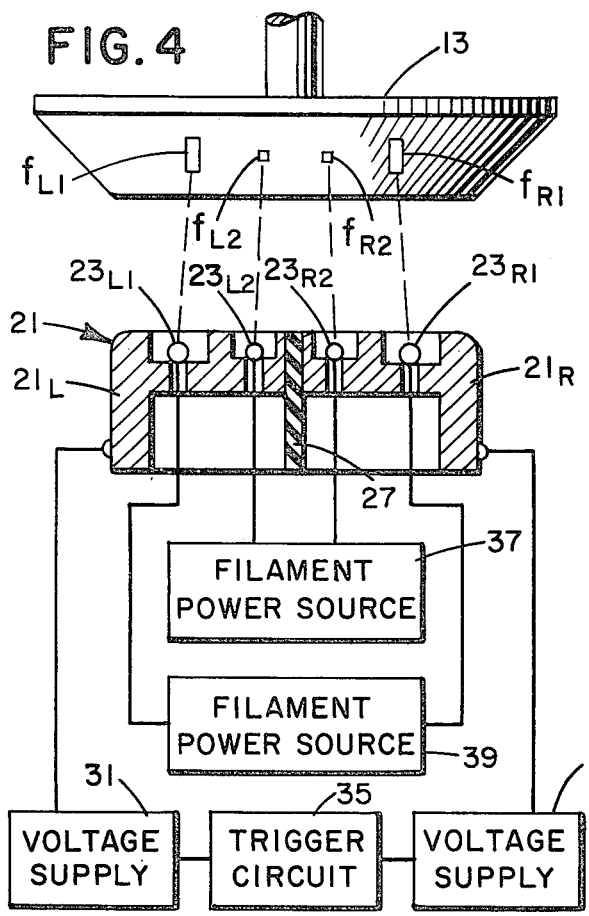
FIG. 4 is a sectional view of the main portion of a stereoscopic X-ray tube embodying a modified form of this invention.

FIG. 4 shows a modified stereoscopic X-ray tube. An insulator 27 electrically divides the focus electrode 21 into the two sections 21L and 21R. Consequently, the electrical operation of section 21L is independent of the operation of section 21R. When a negative bias voltage is applied to the two sections $21_L$ and $21_R$ from voltage supply sources 31 and 33, which are controlled by a trigger circuit 35, an electron beam emitted from any of the filaments 23 is cut-off. On the other hand, when the focus electrode 21 and the filaments 23 are at the same potential, the filaments generate the electron beams. The blocks 37 and 39 designate filament power sources.

In this way, the switching of X-ray radiation is realized by controlling the potential of the focus sections of the focus electrode 21. As a result, the switching can be accomplished within a short period of time so that radiographs of quick movable objects, including a heartbeat, can be made.

Figure 5:
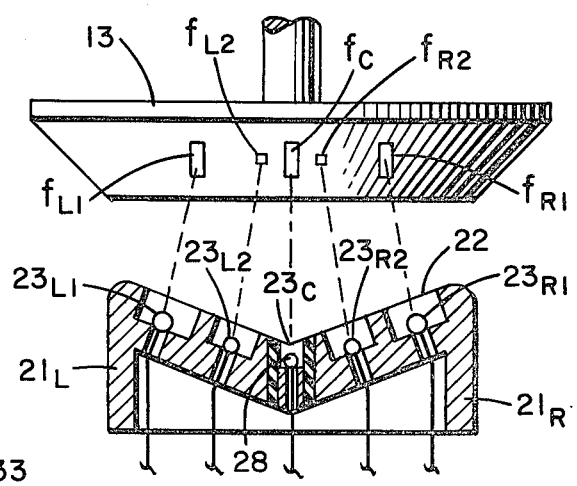
FIG. 5 is a sectional view of the main portion of a stereoscopic X-ray tube embodying another modified form of this invention.

FIG. 5 shows a poortion of a stereoscopic X-ray tube embodying this invention in which there is a center filament 23C. An electron beam emitted from the center filament 23C causes a focal spot FC on the center of the target, as observed from outside of the tube 10. Therefore, one X-ray tube can be used for both stereoscopic and general radiography.

The addition of the center filament on the filament arrangement spreads out the other filament positions from each other. To counteract the spreading out of the filaments and to fucus the electron beams on the target 13, the focus electrode surface 22 facing the target is V-shaped. Consequently, since the distance between the focal spots is reduced by using the V-shape, it is possible to fix the final distance between the focal spots as desired. The filaments 23 are arranged in a line on the surface of the V-shape focus electrode 21 as shown in FIG. 5.

Figure 6:
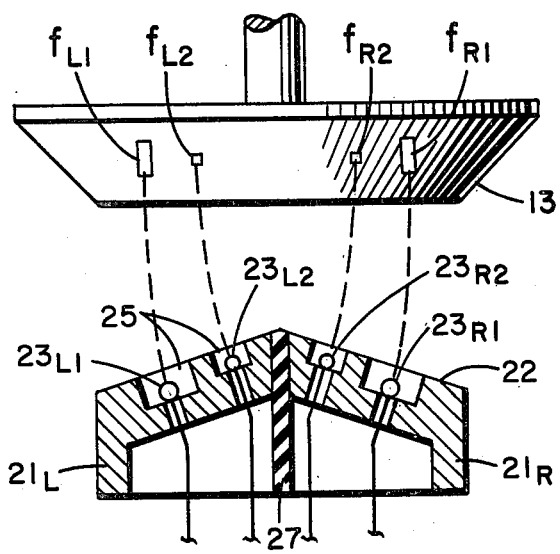
FIG. 6 is a sectional view of the main portion of a stereoscopic X-ray tube embodying a third modified form of this invention.

The focus electrode surface 22 also can be an upside down V-shape as shown in FIG. 6. The focus electrode surface 22 slopes downwardly from its apex. The cavities 25 are located on the downward slope of the surface 22 and filaments 23 are arranged in a line on the surface of the upside down V-shape surface. As shown, the focal spots are formed away from each other. As a result, distances between focal spots are selected by filament positions and the slant or slope of the focus electrode surface 22.

Figure 7:
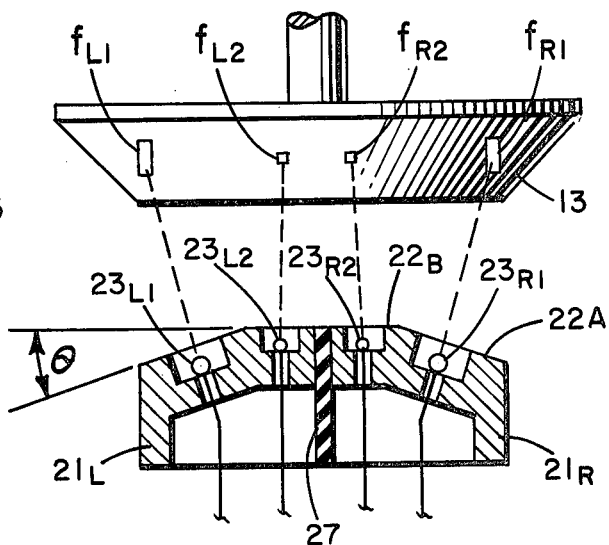
FIG. 7 is a sectional view of the main portion of a stereoscopic X-ray tube embodying a fourth modified form of this invention.

In the modified embodiment as shown in FIG. 7, the focus electrode 21 contains a centrally located surface 22B which is parallel to the target 13. This surface 22B has a pair of filaments forming the smaller size focal spots. The other focus electrode surface 22A, which has another pair of filaments $23_{L1}$ and $23_{R1}$ forming the larger size focal spots $f_{L1}$ and $f_{R1}$, is tilted at an angle θ to the surface 22B. Such a cathode structure provides relatively small focal spots at a small distance from each other on the target 13 and relatively large focal spots at a large distance from each other.

It is to be understood that this invention is not limited to the specific embodiment described above. For example, the cathode structure may have more than two pairs of filaments. It is also to be understood that a stereoscopic X-ray tube according to this invention has effects as follows:

1. the X-ray tube can obtain maximum information by selecting the focal spots properly in accordance with the object to be radiographed;
2. the X-ray tube is applicable to general radiography because of the small distance between focal spots;
3. the X-ray tube is suitable for continuous stereoscopic radiography of objects in fast motion because electron beams from a pair of filaments are switched alternately between two focal spots by controlling the potential on a focus electrode; and
4. the X-ray tube does not require a grid for absorbing scattered X-rays because the film is spaced apart from the object for magnification radiography. Therefore, the skin dose to the patient can be reduced.

We claim:

1. A stereoscopic X-ray device comprising:
an evacuated envelope;
a target within said envelope; and
electron beam means within said envelope for directing electron beams on said target to form at least two pairs of focal spots on said target to generate X-rays, said pairs of focal spots being spaced apart on said target, said electron beam means including first and second filament means, said first filament means having a size larger than said second filament means for forming a first pair of focal spots having a larger size than a second pair of focal spots, said second pair of focal spots being formed by said second filament means and positioned between said first pair of focal spots on said target.

2. A stereoscopic X-ray device according to claim 1 wherein said electron beam means comprises cathode means for generating at least two pairs of electron beams directed onto said target to form said focal spots thereon, said cathode means comprising at least two pairs of electron emitting filaments arranged on a focus electrode, the first pair of said filaments forming said one pair of larger size focal spots and the second pair of said filaments, situated between said first pair of said filaments, forming said second pair of focal spots.

3. A stereoscopic X-ray device according to claim 2 wherein said focus electrode is divided into two sections by an insulator, each of said sections containing filaments which generate electron beams to form focal spots of different size on said target.

4. A stereoscopic X-ray device according to claim 2 wherein said cathode means further comprises a filament at the center portion of said focus electrode.

5. A stereoscopic X-ray device according to claim 2 wherein said focus electrode is cup-shaped.

6. A stereoscopic X-ray device according to claim 2 wherein each of said filaments is situated in a cavity formed on the surface of said focus electrode.

7. A stereoscopic X-ray device according to claim 2 wherein said filaments are arranged in a line on a V-shaped surface of said focus electrode.

8. A stereoscopic X-ray device according to claim 2 wherein said filaments are arranged in a line on an upside down V-shaped surface of said focus electrode.

9. A stereoscopic X-ray device according to claim 2 wherein said focus electrode has a surface facing said target, said surface comprising a central portion substantially parallel to said target containing said second pair of filaments and a sloping portion sloping away from said target, said sloping portion containing said first pair of filaments.

* * * * *